(12) United States Patent
Krenn et al.

(10) Patent No.: US 10,180,381 B2
(45) Date of Patent: Jan. 15, 2019

(54) ROTARY RHEOMETER

(71) Applicant: ANTON PAAR GMBH, Graz-Strassgang (AT)

(72) Inventors: Michael Krenn, Zettling (AT); Andreas Triebl, Leutschach (AT)

(73) Assignee: Anton Paar GmbH, Graz-Strassgang (AT)

( * ) Notice: Subject to any disclaimer, the term of this patent is extended or adjusted under 35 U.S.C. 154(b) by 204 days.

(21) Appl. No.: 15/156,360

(22) Filed: May 17, 2016

(65) Prior Publication Data

US 2016/0341647 A1 Nov. 24, 2016

(30) Foreign Application Priority Data

May 20, 2015 (AT) .............................. A 50408/2015

(51) Int. Cl.
*G01N 11/14* (2006.01)
*G01L 1/26* (2006.01)

(52) U.S. Cl.
CPC .............. *G01N 11/142* (2013.01); *G01L 1/26* (2013.01); *G01N 2203/0094* (2013.01); *G01N 2203/0204* (2013.01)

(58) Field of Classification Search
CPC ......... G01N 11/142; G01N 2203/0094; G01N 2203/0204; G01L 1/26
USPC ....................................................... 73/54.31
See application file for complete search history.

(56) References Cited

U.S. PATENT DOCUMENTS

| | | | | |
|---|---|---|---|---|
| 8,453,496 | B2 * | 6/2013 | Lauger | G01N 11/142 |
| | | | | 73/54.28 |
| 9,702,809 | B2 * | 7/2017 | Wolf | G01N 19/02 |
| 2008/0022758 | A1 * | 1/2008 | Cottais | G01N 11/142 |
| | | | | 73/54.32 |
| 2010/0269571 | A1 * | 10/2010 | Raffer | G01N 11/142 |
| | | | | 73/54.28 |

FOREIGN PATENT DOCUMENTS

| AT | 508706 B1 | 6/2011 | |
|---|---|---|---|
| CN | 1885005 A | * 12/2006 | |
| WO | WO 2015069633 A1 | * 5/2015 | ............... G01N 3/02 |

* cited by examiner

*Primary Examiner* — Son Le
*Assistant Examiner* — Marrit Eyassu
(74) *Attorney, Agent, or Firm* — Laurence A. Greenberg; Werner H. Stemer; Ralph E. Locher

(57) ABSTRACT

A rotary rheometer has two measurement parts which delimit a measurement gap and can be moved relative to one another in a predetermined movement direction by an adjustment device. At least one switching unit is provided, which responds to changes in a force flow in a force circuit of the rotary rheometer delimited by the measurement parts and has switching contacts for the activation of an adjustment device, which stops the adjustment device when a predetermined limit force value is exceeded for the force flow in the positive or negative direction, optionally without relative movement of the measurement parts, or with the measurement parts remaining in the same position.

18 Claims, 6 Drawing Sheets

ROTARY RHEOMETER

CROSS-REFERENCE TO RELATED APPLICATION

This application claims the priority, under 35 U.S.C. § 119, of Austrian application AT A50408/2015, filed, May 20, 2015; the prior application is herewith incorporated by reference in its entirety.

BACKGROUND OF THE INVENTION

Field of the Invention

The invention relates to a rotary rheometer.

SUMMARY OF THE INVENTION

The object of the invention is above all, for rheometers and therefore also for viscosimeters which do not have their own built-in normal force measurement, to provide normal force limitation which keeps the measurement gap constant and prevents damage in the event of excessively high forces. In the case of the invention, viscosimeters are regarded as equivalent to rheometers.

By definition, rheology deals with the deformation and flow behavior of substances. Rotary rheometers are measuring instruments for studying the rheological properties of different material samples. Viscosimeters are special rheometers for determining viscosity. In this case, the measurement sample to be studied is introduced into a generally narrow measurement gap between two measurement parts, the two measurement parts are rotated and/or oscillated relative to one another, and the material sample is subjected to a shear load between the measurement parts. Elastic material functions are additionally obtained from the axial forces which act perpendicularly to the shear plane in cone/plate and plate/plate rheometers or similar arrangements. In this case, a multiplicity of further possible measurement part geometries are known. Rotary rheometers make it possible to combine a multiplicity of different test runs in which either the shear stress, the shear deformation or the shear rate can be predetermined. Rotary rheometers may in principle have different embodiments with a measurement motor, a rotation motor and a separate measurement motor, or the combination of two measurement motors, and are described for example in Austrian patent AT508706 B1, corresponding to U.S. Pat. No. 8,453,496.

The torque determination in the rotary rheometer may be carried out with (measurement) motors configured for driving and for torque determination, or alternatively by two separate motor units for drive/rotation and for torque determination, which are respectively assigned to one of the measurement parts. Depending on the instrument type, the upper measurement part or the lower measurement part, for example a measurement cup, in this case rotates. The resulting torque and/or the phase angle are determined. Furthermore, a double motor system with two measurement motors is also known, for example Austrian patent AT 508 706 B1. In addition to this, different systems for determining the normal forces (axial forces) occurring are known.

FIG. 1 represents a known embodiment of a rotary rheometer. The medium sample to be measured lies on the lower measurement part 30 (here a plate). A measurement gap S is formed by lowering an upper measurement part 20 into contact with the sample to be studied.

The rheometer shown here by way of example has a measurement motor M, which rotates or drives in rotating oscillation a measurement shaft 22 and the upper measurement part 20 connected thereto. In this case, the relationship between the torque on the measurement shaft 22 and the power consumption of the measurement motor M is accurately known or can be determined by calibration. Different measurement systems and maximally low-friction bearing arrangements make it possible to determine the rotation angle and rotation speed. All the values are available in an evaluation unit, which is not represented.

The rheological characteristics of the medium sample are determined in the evaluation unit from the torque or from the supply parameters, in particular from the electricity consumption of the measurement motor M and/or from the frequency and/or from the phase angle of the measurement shaft 22 and the gap data while taking into account measurement geometry data of the measurement parts and the temperature.

The determining factors for the measurement accuracy in the rheometer or viscosimeter are, besides precise determination of the torque and the stability of the ambient conditions, maximally friction-free mounting of the drive and/or measurement shafts, and in particular also the stiffness of the stand. In order to measure the respective instantaneously acting torque with minimal frictional and tensile forces, for example magnetic and air bearings for the rotating components are known.

The actual distance of the two measurement parts from one another, or the height or thickness of the gap S, in this case also has a great influence on the measurement accuracy. The measurement motor and the measurement parts lie at an adjustable axial distance from one another, which is kept constant during the measurement, on a stand 32 or frame 33. In this case, at least one of the measurement parts is actuated by an optionally automatic setting unit, or adjustably carried by setting parts.

Other features which are considered as characteristic for the invention are set forth in the appended claims.

Although the invention is illustrated and described herein as embodied in a rotary rheometer, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
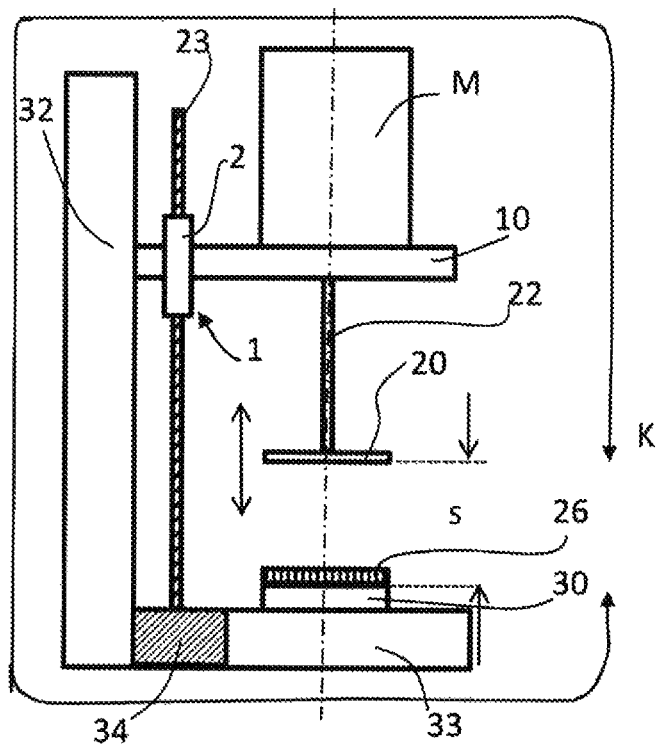
FIG. 1 is a diagrammatic illustration of a rheometer according to the prior art.

Referring now to the figures of the drawings in detail and first, particularly to FIG. 1 thereof, there is shown a conventional type of adjustment of a gap height S. A drive or forward feed motor 34 mounted on a stand 32 displaces a measurement part 20 carried by a further motor M on an upper setting part or carrier 10 by means of an adjustment unit 1, formed by a screw spindle 23 and screw nut 2, relative to the lower measurement part 30, which is carried by a base plate 33. The sample to be studied is introduced between the two measurement parts 20, 30 and optionally trimmed after the gap adjustment. For the gap height adjustment, the regulation of the forward feed motor of the spindle 23 is carried out by means of the values measured by a contactlessly operating distance or path or length measurement unit arranged on the spindle 23. Length measurement units known per se, for example potentiometers, incremental path transducers, inductive measurement pickups or dial gauges, respectively measure the distance between the measurement parts 20, 30 and/or between the spindle nut 2 and a fixed point on the stand 32 or on the base plate 33 or other fixed points. The measurement of the actual distance s may be carried out both absolutely by corresponding calibration for the respectively used measurement geometry on the height, forward feed and adjustment system, or on the setting unit, and relatively, i.e. on the basis of a gap zero point respectively determined by suitable methods, for example by the torque increase or normal force increase when the measurement parts come to touch one another. The use of stepper motors in order to carry out controlled positioning of the setting parts relative to one another, without the need for distance measurement, is also known.

Under constant ambient conditions, predetermined gap heights S can therefore be approached with micrometer accuracy, and at the same time the required forward feed in the mm or cm range for introduction of the sample medium into the measurement gap, or for changing the measurement parts, can be achieved.

Nevertheless, any differently designed precise mechanical linear forward feed may also be used, for example linear motors, pneumatically driven adjustment devices, Uhnig nut drives, and the like, in order to be able to introduce the sample into the measurement gap S by lowering and raising the lower measurement part 30 and/or the upper measurement part 20 and establishing the desired measurement gap between the measurement parts 20, 30.

In a rheometer having a stand, and above all in automated gap systems, the problem arises that when the measurement system is immersed in the sample and when the measurement system is extracted from the sample, different normal forces act on the bearing of the measurement motor. These forces likewise depend on the viscosity of the sample, as well as on the nature of the measurement system and the displacement speed. In the event of a displacement speed selected incorrectly by the user, a mechanical overload may be triggered, the drive may be blocked, or the measuring apparatus may even be damaged. In all these cases, the measurement gap S is modified, the sample must be taken out of the measuring instrument, and the latter must be re-referenced.

In many cases, rheometers have normal force measurement devices which make it possible not only to study the torques acting, which act against the shear load because of the sample viscosity, but also to measure the normal forces acting perpendicularly to the shear load. These forces almost always occur because of the elastic components of real viscoelastic samples. A wide variety of variants for normal force measurement are known in the prior art, for example contactlessly operating normal force sensors located in the air bearing of a rotary rheometer.

Economical viscosimeters or rheometers, for example for monitoring and standard characterization of samples in production processes, are however often configured without normal force measurement for cost reasons. In this accuracy class, the measurement drives are for example configured with a ball bearing or favorable air bearings.

The object of the invention is to develop a system which can record normal forces in the positive and/or negative direction up to a maximum limit force without significant or no negligible movement of the measurement parts, and therefore without a substantial measurement gap change, i.e. it holds the rheometer entirely stiffly but, when this limit force is exceeded, directly opens a contact and therefore makes the occurrence of a normal force exceeding the limit force detectable. In this way, the rheometer can stop the displacement movement until the normal force is reduced below the limit value. Once the normal force has decreased below the limit value again, the contact is closed and the mechanical position is again absolutely identical to that before the opening.

Since one key element for accurate characterization of the sample is the consistency of the measurement gap, all safety devices must essentially be configured without travel, and the measurement gap between the measurement parts must be kept constant.

For example, the normal force discontinuity when reaching the contact point of the upper measurement part with the sample is used to establish when the two measurement parts 20, 30 have come in contact with the sample when being brought together and therefore that the approach of the two measurement parts must be slowed. In particular, viscoelastic samples with a high elastic component, for example polymer melts, asphalt, chocolate, etc. are not compressed in shape until they are between the two measurement parts 20, 30 and possibly protruding sample edges are trimmed after the desired measurement gap width has been adjusted. If the rheometer has a normal force measurement unit, it is ensured by means of the latter that the sensitive components, in particular bearings, etc. of the rheometer are not damaged. The outline profile, represented in FIGS. 2A, 2B, of the normal forces occurring during the approach may be used directly by the control and regulation unit to regulate the motor speed of the adjustment mechanism. The approach takes place until contact with maximum speed, while after contact the measurement parts only move toward one another slowly. In this case, the maximum permissible normal force which may occur may be stored as a threshold value in the control and evaluation unit.

Figure 2A:
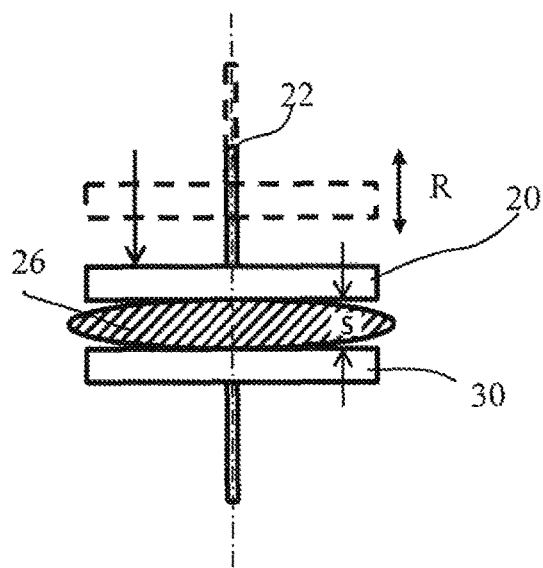
FIG. 2A is an illustration of measurement parts.
Figure 2B:
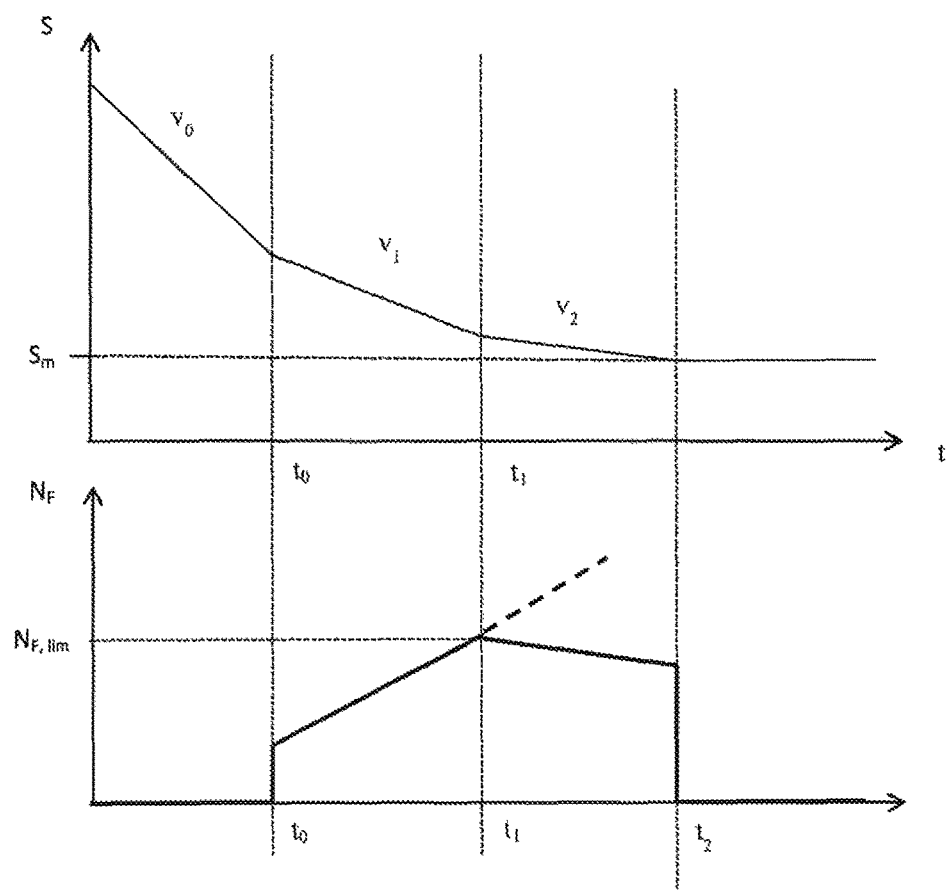
FIG. 2B is a graph illustrating a variation of a normal force and of a distance between the two measurement parts over time.

FIGS. 2A, 2B schematically represents the variation of the normal force NF and of the distance S between the two measurement parts 20, 30 when approaching or bringing together the measurement parts as a function of time t.

The two measurement parts 20, 30 of the rheometer, here a plate/plate measurement system, are brought toward one another in the direction R. The distance between the two measurement parts 20, 30 is selected at the start of the test so that the sample can be introduced well between the measurement parts, and the distance between the measurement parts is therefore large. The schematic diagrams represent the variation of the gap width of the measurement gap S between the plates and the measured or occurring normal force between the measurement parts 20, 30. The first section shows rapid approach of the two measurement parts until the time $t_0$—in this case, the normal force increases abruptly. After this time, the sample surface is in contact with the two measurement parts. The further approach generally only takes place more slowly, in order to introduce the sample uniformly between the measurement parts. If at a time (here $t_1$) the highest permissible normal force is exceeded, then the adjustment speed can be reduced again by the control and regulation unit, or the adjustment device. The approach takes place with $V_3$ or is stopped, in order to allow adaptation of the sample to the gap width. When the desired (measurement) gap width $S_m$ is reached, the sample may optionally be trimmed and the measurement may be started. The normal force profiles shown may naturally also not extend linearly, depending on the sample, and are represented here only by way of example.

A further problematic case is the limitation of the forces occurring when the two measurement parts are moved away from one another after the test has been carried out.

Figure 3A:
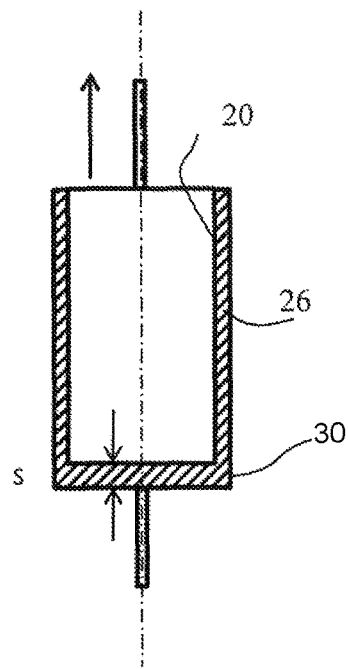
FIG. 3A is an illustration of a cylindrical measurement system.
Figure 3B:
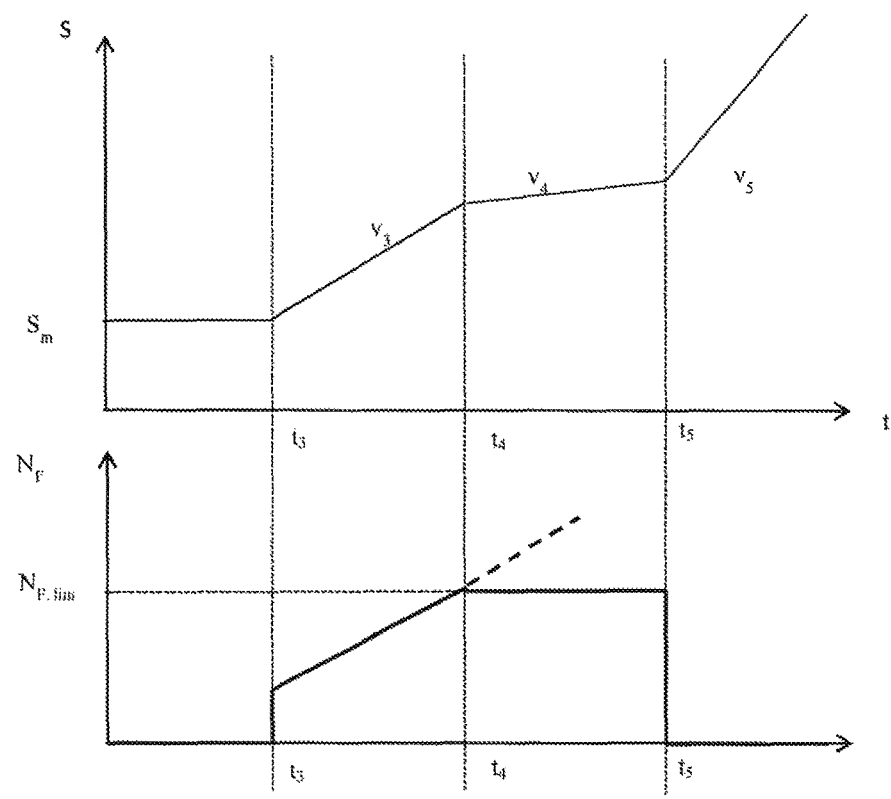
FIG. 3B is a graph illustrating a variation of a normal force and of a distance between the two measurement parts over time.

FIG. 3 shows such an arrangement with a cylindrical measurement system having two concentrically arranged cylindrical measurement parts 20, 30, which are moved apart from one another after the measurement. The variation in the normal force NF and the distance between the two measurement parts 20, 30 is represented schematically as a function of time t.

Many studied samples, for example after the hardening of rubber, solidification of chocolate, etc. adhere to the measurement parts. In particular when using cylindrical measurement systems, with naturally large contact areas between the measurement part surface and the sample, the measurement system may be damaged. When there is a normal force measurement, the system reduces the displacement speed of the carrier of the measurement part because of the negative normal forces occurring.

After the end of the measurement with a defined distance of the measurement parts $S_m$, at time $t_3$ the separation of the measurement parts from the sample begins by movement with the speed $V_3$. If the normal forces in this case increase because of effects, for example adhesion, and exceed the adjusted limit force (time $t_4$), the speed of the drive is adapted ($V_4$) or the drive is stopped. When the sample has been fully separated from one of the measurement parts or contact with the sample residues adhering to the two measurement parts is broken, movement may continue at maximum speed. At time $t_5$ NF decreases to 0.

Here again, the profiles of the distance between the measurement parts 20, 30 and the variation of the normal force NF are represented schematically. Actual profiles show different functional dependencies depending on the sample properties.

Another problem is the extremely high normal forces occurring for many samples, which may arise during the conduct of a test, for example thermal regulation of the sample, shear thickening or the like, and require immediate interruption of the measurement.

If an economical rheometer or viscosimeter, for example for standard characterization, has not implemented any normal force measurement, apart from the sensitive measurement and bearing parts, an automatic or motor-controlled stand which may be used may also be damaged by the overloads occurring, when the stepper motor cannot be throttled or stepped down by the motor control.

Hitherto, this problem has been resolved by having to select extremely slow speeds for automatic movement with the stand, and an unnecessary time loss has therefore had to be tolerated even for quality measurements.

Even with manual adjustment on the stand, the sensitive motor bearing may in this case suffer damage when the adjustment mechanism of the stand is moved further despite high forces occurring.

If precise force measurement or a limiter switch were installed in this case, the measurement gap must not be influenced. Particularly when moving the measurement parts toward one another, the switching mechanism must generate no delay in the triggering, since otherwise the gap geometry could be modified.

Because of the hysteresis which any switch has for its triggering behavior, conventional switches entail a variation of the gap due to the normal force occurring. The gap, however, must not vary as a function of the forces occurring, especially when the measurement parts are being moved toward one another.

According to the invention, these problems are resolved in a rotary rheometer of the type mentioned in the introduction. According to the invention, at least one switching unit is provided, which responds to changes in the force flow in the force circuit, delimited by the measurement parts, of the rotary rheometer and has switching contacts for the activity of the adjustment device, which stops the adjustment device when a predetermined limit force value is exceeded for the force flow in the positive or negative direction, optionally without relative movement of the measurement parts, or with the measurement parts remaining in the same position.

For precise switching, it is advantageous that the contact parts of the switching contact are arranged movably relative to one another in a direction which extends parallel to the direction of the relative movement of the measurement parts in the course of their adjustment, or has a component extending parallel to this movement direction.

A mechanically advantageous structure is obtained when the two contact parts of the respective switching contact respectively lie on one of two members of the force circuit of the rotary rheometer which can be moved relative to one another or are structurally independent of one another or can be separated from one another, and at least one spring unit is provided, with which these two members and the contacts of the switching contact can be pressed onto one another or toward one another by spring force and are held in this position.

Depending on the intended use of the rheometer, it is possible that the switching contact is arranged on individual components of the force circuit of the rotary rheometer, preferably a carrier or a carrier plate of the measurement or drive motor, along a measurement shaft, along a drive spindle of the adjustment device or along the holder for the measurement or drive motor, or respectively between the individual components or in the connection or transition region from one component to the other.

For the structure of the rotary rheometer, it is expedient that the force circuit of the rotary rheometer contains as components a stand, a frame, a carrier for the drive or measurement motor and the measurement part and the measurement shaft, and the adjustment device for height adjustment of the measurement part or the spindle and/or its drive.

A simple and accurate structure is obtained when the contact parts of the switching contact, which interact for switching off or stopping the adjustment device, and are optionally formed as contact surfaces, lie on physically separable and independently movable members or components of the force circuit, which are pressed with a spring force, in particular parallel to the component of the normal force occurring in the sample and optionally measured, in the direction in which the measurement gap is variable and adjustable, or in which the measurement parts can be moved toward one another or away from one another.

In order to avoid damage, it is advantageous that the adjustment device abruptly terminates the adjustment movement of the measurement parts relative to one another when the switching contact is opened and/or, when the carrier is formed at least with two members. The respective members which lie successively in the force circuit respectively being pressed against one another by at least one spring unit with a predetermined spring force, and in that when a separating force exceeding the spring force acts on the members the two members pressed against one another can be removed from one another and at the same time the contact parts of the switching contact can therefore be separated from one another.

A rheometer which can be used advantageously in practice and is constructed simply with a nut mounted adjustably in height on the drive spindle, is obtained when the nut carries a preferably annular contact member with an upwardly projecting contact part, a contact part preferably formed by a contact ring lying above the contact part and being connected to a clamp sleeve which carries a clamping ring on its lower end, a coil spring with a predetermined spring force being arranged between the clamping ring and the carrier of the drive or measurement motor or of the measurement shaft, and a further coil spring with a predetermined spring force being arranged between the nut and the clamping ring and/or when the carrier carries an upwardly projecting contact part, in that a contact member with a downwardly projecting contact part, which can be applied from above onto the contact part carried by the carrier, is arranged above the carrier, which contact part is carried by a clamping sleeve which carries a clamping ring at its lower end, a coil spring with a predetermined spring force being arranged between the clamping ring and the carrier of the drive or measurement motor or of the measurement shaft, and a further coil spring with a predetermined spring force being arranged between the nut and the clamping ring.

A structure which is advantageous for the geometry of the rheometer is obtained when the coil spring encloses the further coil spring and optionally extends below the switching contact, and/or in that the clamping sleeve lies between the coil spring and the further coil spring, and/or in that the further coil spring encloses the spindle, and/or when the contact parts are loaded with leaf or helical or coil springs, the spring force of which acts in the direction of the opening and closing movement of the contact parts or has a spring force component acting in this direction.

In practice, it is very expedient that in order to detect the by at least one measurement part in the course of its adjustment by a force exerted by the sample, in addition to the switching unit or switching contacts responding to the force flow in the force circuit, a device for measuring the normal force FN exerted by the sample and directed positively or negatively with respect to the direction of the force flow is provided.

For the guidance of the measurement method, it is advantageous that the lifting spring and the lowering spring are respectively prestressed with a prestressed force or a limit force value, which corresponds to the weight of the components or apparatus to be carried of the rotary rheometer and a predetermined force value. The predetermined force value corresponds to a force value exerted by the sample onto the measurement part in the positive and negative directions of the force flow and still regarded as tolerable.

According to the invention, the switching unit may be a spring system, prestressed on one or both sides against a stop, with switching contacts. Therefore, no movement takes place in the detection system until the triggering by exceeding the limit force value. When the limit force value is exceeded, the switching contact, which may be produced electrically via the contact surfaces of the prestressed spring units, is broken by a minimum excursion in the μm range.

By application of the spring units, for example helical springs, leaf springs or the like, the electrical switching contact can be prestressed against the limit force value, or the maximum permissible force NF. The spring(s) arranged for this purpose press the prestressed components or members of the rheometer against one another along the force circuit and establish there an electrical contact on the mutually touching contact surfaces. If the force occurring exceeds the limit implemented by the stiffness of the springs, the contact is broken and this interrupts the movement of the displacement unit, for example the current supply of the stepper motor.

This pre stressed switching contact may be installed at different positions in the force circuit of the rheometer. In this case, the two contact parts of the switching contact may be installed in any desired way separately in the force circuit of the rheometer, or alternatively the contact parts are installed preferably mirror-symmetrically with respect to the spindle or the measurement shaft together with the spring elements in the rheometer.

Figure 4:
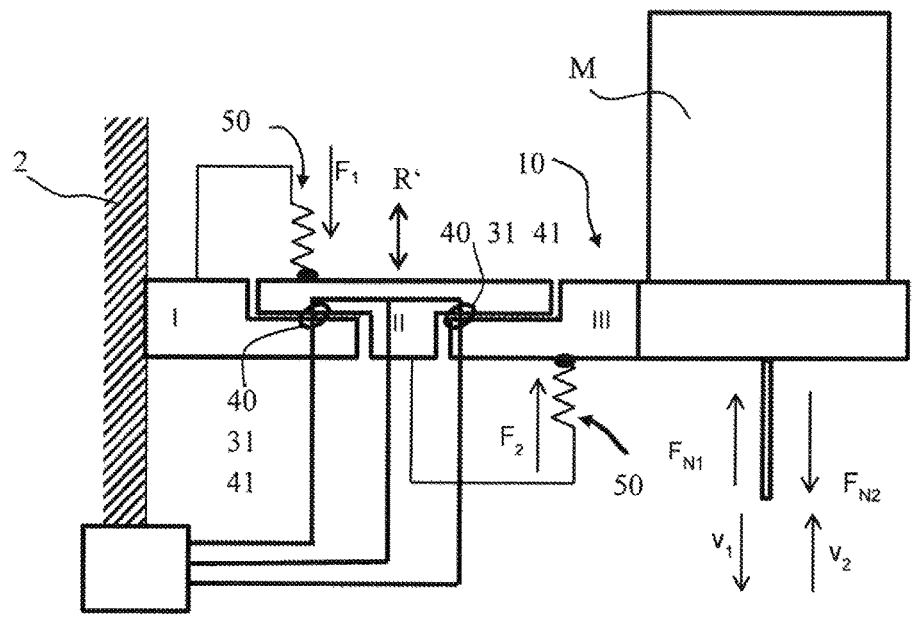
FIG. 4 is an illustration of a first embodiment of a rheometer according to the invention.

FIG. 4 shows by way of example an alternative embodiment of the invention in a schematic section through the carrier arm or carrier 10 of the rheometer with a spring unit acting in both directions, i.e. upward and downward. The carrier arm or carrier 10 is divided overall into three segments or members I, II, III. The segments I, II, III are pressed firmly against one another by the spring force of the pre stressing spring units 50, and the overall stiffness of the rheometer therefore remains unaffected until the limit force value is exceeded.

One spring unit 50 presses the segment II, configured as a T-shaped carriage with the force F1 against the left-hand carrier arm part I, and a second spring element 50 presses the segment III with the force F2 against the carrier arm part, or the segment II. At the same time, contact parts 31, 41 of switching contacts 40 are pressed against one another.

In the case of the two switching contacts 40, the electrical contact parts 31, 41 are kept closed by the spring force and the current circuit or supply circuit of the displacement mechanism of the adjustment device 1 can be switched with these switching contacts.

If the carrier arm or carrier 10 is now moved with the upper measurement part 20 and the measurement motor M with the speed v1 onto the lower measurement part 30, then beyond the adhesion to the sample, since the sample is in contact with the two measurement parts 20, 30, normal forces FN1 occur against the movement direction R'. Until the triggering force or limit force value FN1=−F1 is reached, the stand 32 and the frame 33 and the displacement device 1 remain unaffected by the forces occurring.

When the force limit value is reached, the spring force is equalized and the contact surfaces of the contact parts 31, 41 are lifted off one another, and the activity of the displacement device 1 is interrupted with the least possible displacement movement and without a time delay or hysteresis by opening the switching unit 40.

The same applies for the movement of the carrier 10 in the opposite direction with the speed v2 and the forces FN2 occurring in the opposite direction.

Until the triggering force or limit force FN2=−F2 is reached, the stand 32 and the frame 33 and the displacement device 1 remain unaffected by the forces occurring; the spring-loaded contact parts 31, 41 remain pressed against one another.

It is also possible to divide the carrier arm or carrier 10 only once. Correspondingly, it is then only possible to switch off the adjustment unit when the normal force FN1 or FN2 occurs.

In order to be able to implement the inventive principle, the spring unit 50 schematically represented here may be produced with any desired spring geometry; for example, leaf springs or coil springs may be used.

A principle for normal force limitation is therefore implemented without explicit or actual measurement of the normal force. This purely mechanical alternative embodiment is robust and economical, and operates reliably.

In the context of the invention, a spring unit 50 is intended to include all elements which can press the contact surfaces 31, 41 of the switching contacts 40 against one another with a defined prestress. Besides mechanical spring systems, it is also possible to select pneumatic cylinders and/or electromagnetic springs and/or permanent magnets as alternative implementation variants.

Figure 5:
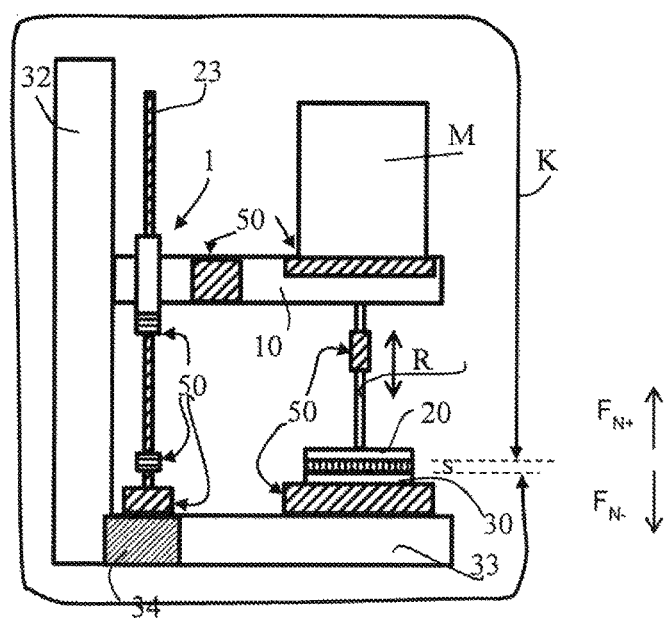
FIG. 5 is an illustration of a second embodiment of the rheometer.

FIG. 5 schematically shows a rheometer arrangement having a stand 32 and a frame 33, as well as a measurement motor M which is mounted adjustably in height on the stand 32 while being connected thereto by the carrier arm or carrier 10.

By way of example, different installation variants of the switching unit and of the spring units 50 in the force circuit K of the rheometer are represented here. If the measurement gap S is closed and the two measurement parts 20, 30 are in contact with the sample, the force circuit K represented in outline is closed. The stand 32 and the measurement motor M are configured to be as stiff as possible, so that the measurement gap S is not modified by the forces occurring in the components that convey force. The spring units 50 provided according to the invention may be installed at different positions in this force circuit K. In FIG. 5, some of the relevant positions are represented schematically by the hatched surfaces, namely directly in the region of the stand 32, linearly in the carrier arm or carrier 10 or rotationally symmetrically around the motor support M', or close to the two measurement parts 20, 30. If a spring unit 50 is installed in the measurement shaft 22, it is necessary to ensure that the torque measurement is not influenced by the spring system, and the embodiment should be rotationally symmetrical, which also applies to installation on the spindle 23.

If adjustment is merely carried out manually, then instead of stopping the adjustment unit by the switching unit it is possible to emit a warning signal, and the manual adjustment is ended.

Figure 6:
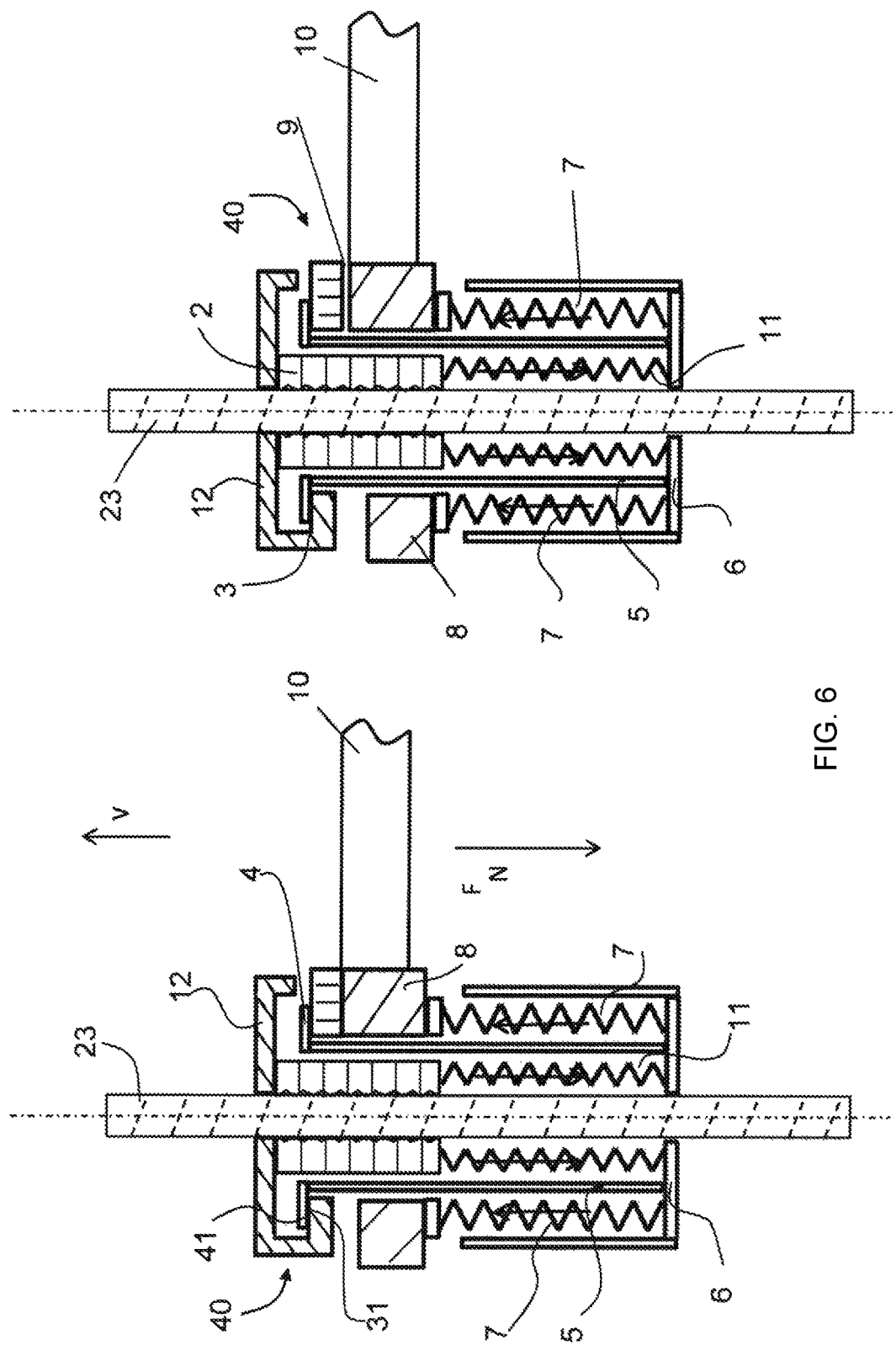
FIG. 6 is an illustration of a first embodiment of a switching unit assembly.
Figure 7:
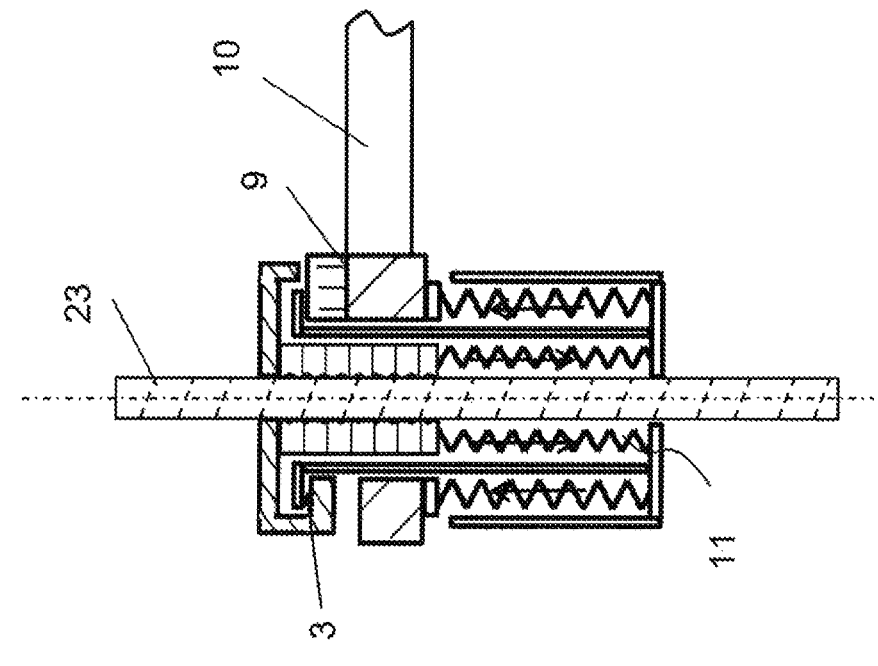
FIG. 7 is an illustration of a second embodiment of the switching unit assembly.
Figure 7:
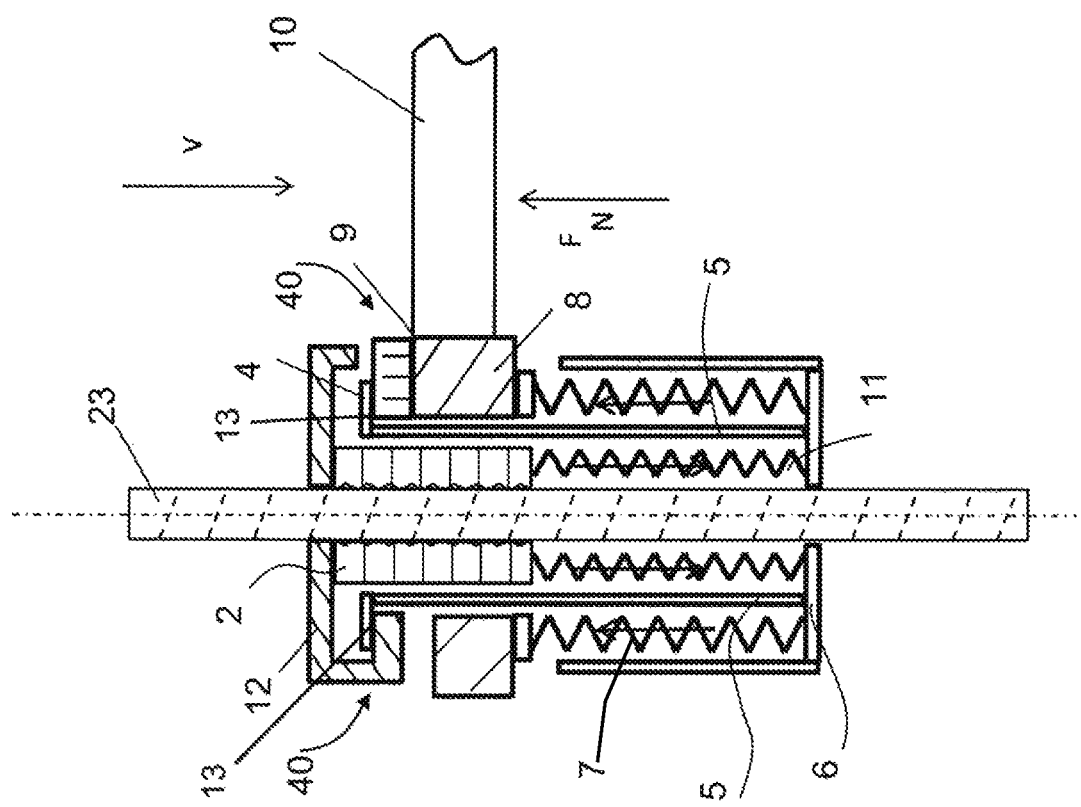

Preferably, the normal force limitation for both movement directions R is carried out in a combined member, in which two spring units 50 act against one another and prestress the contact surfaces 31, 41 against the two force directions R', as is represented in FIGS. 6 and 7. Naturally, the normal force limitation may also be configured in only one active direction, or the two active directions may be implemented separately of one another in the force circuit K of the rheometer.

A preferred alternative embodiment for the installation of a switching unit, or of switching contacts 40, in the spindle 23 of a linear drive for the carrier 10 is represented in FIGS. 6 and 7.

The rotational movement of the spindle 23 is converted by means of the nut 2 into a vertical movement with the speed v, the rotation of the nut 2 optionally being prevented by an overload pin, which is for example guided in a driver jaw or holding ring 8.

If the nut 2 moves upward according to FIG. 6, then the lifting force of the nut 2 acts via the fixing ring or annular contact member 12, the contact surface 31 of the NF-minus contact 3, the contact ring 4 with the contact surface 41, the clamping sleeve 5 and the clamping ring 6 on a lifting spring 7, for example a coil spring, which is braced via the driver jaw or holding ring 8 on the driver plate or the carrier 10. If the carrier 10 is blocked against a vertical movement upward and the lifting force of the nut 2 exceeds the pre-stressed force of the lifting spring 7 less the intrinsic weight of the apparatus to be lifted, i.e. the carrier 10 with the motor M as well as the measurement shaft 22 and the upper measurement part 20 and any other entrained members, the NF-plus contact 9 opens.

The movement of the nut 2 upward acts against a normal force—FN. This force action is transmitted via the carrier 10 and the holding ring 8 to the lifting spring 7, which acts between the clamping ring 6 and the nut 2. With opening of the NF-plus contact 9, the adjustment movement of the carrier 10 ends abruptly. In FIG. 6, the operational position is represented on the left and the position in which the displacement unit 1 is stopped is represented on the right.

If the nut 2 moves downward according to FIG. 7, then the lowering force of the nut 2 acts on the lowering spring 11, which is braced via the clamping ring 6, the clamping sleeve 5, the contact ring 4, the NF-plus contact 9 via the driver jaw 8 on the carrier 10. If the carrier 10 is blocked against a vertical movement downward and the lowering force of the nut 2 exceeds the pre stressed force of the lowering spring 11 plus the intrinsic weight of the apparatus to be lifted by a predetermined force value, the NF-minus contact 3 is opened.

The movement of the nut 2 downward acts against a normal force FN. This force action is transmitted via the carrier 10, the driver jaw 8, the NF-plus contact 9, the contact surface 13, the clamping sleeve 5 and the clamping ring 6, and acts against the predetermined pre stressed force of the lowering spring 11.

The force flow may also change without the measurement parts 20, 30 executing a movement.

The invention claimed is:

1. A rotary rheometer, comprising:
    an adjustment device;
    two measurement parts delimiting a measurement gap and can be moved relative to one another in a predetermined movement direction by said adjustment device;
    a force circuit delimited by said measurement parts; and
    at least one switching unit responding to changes in a force flow in said force circuit, said switching unit having switching contacts for an activation of said adjustment device, said switching unit stopping said adjustment device when a predetermined limit force value is exceeded for the force flow in a positive direction, without relative movement of said measurement parts, or with said measurement parts remaining in a same position, said at least one switching unit responding to changes in the force flow in said force circuit by said switching unit stopping said adjustment device when the predetermined limit force value is exceeded for the force flow in a negative direction, without the relative movement of said measurement parts, or with said measurement parts remaining in the same position.

2. The rotary rheometer according to claim 1, wherein said switching contacts each have contact parts disposed movably relative to one another in a direction which extends parallel to the predetermined movement direction of a relative movement of said measurement parts in a course of their adjustment.

3. The rotary rheometer according to claim 2,
wherein said force circuit has two members;
wherein said contact parts include two contact parts for each of said switching contacts respectively lying on one of said two members of said force circuit which can be moved relative to one another or are structurally independent of one another or can be separated from one another; and
further comprising at least one spring unit with which said two members and said contact parts of said switching contacts can be pressed onto one another or toward one another by a spring force and are held in position.

4. The rotary rheometer according to claim 2, wherein:
said force circuit has physically separable and independently movable members; and
said contact parts of said switching contact interact for switching off or stopping said adjustment device, said contact parts having contact surfaces lying on said physically separable and independently movable members of said force circuit, which are pressed with a spring force, parallel to a component of a normal force occurring in a sample and measured, in the predetermined movement direction in which the measurement gap is variable and adjustable, or in which said measurement parts can be moved toward one another or away from one another.

5. The rotary rheometer according to claim 2, wherein:
said adjustment device has a drive spindle;
at least one spring unit; and
said force circuit has a carrier carrying a drive and measurement motor and a measurement shaft of one of said measurement parts being an upper-lying measurement part, said carrier is mounted adjustably in height on said adjustment device via said drive spindle, said carrier is formed from at least with two members lying successively in said force circuit respectively being pressed against one another by said at least one spring unit with a predetermined spring force, and in that when a separating force exceeding a spring force acts on said members (I, II; II, III) said two members (I, II; II, III) pressed against one another can be removed from one another and at a same time said contact parts of at least one of said switching contacts can therefore be separated from one another.

6. The rotary rheometer according to claim 2, said contact parts are loaded with springs selected from the group consisting of leaf springs, helical springs and coil springs, a spring force of said springs acts in the predetermined movement direction of an opening and closing movement of said contact parts or has a spring force component acting in the predetermined movement direction.

7. The rotary rheometer according to claim 2, wherein:
said force circuit has members; and
said contact parts are formed by parts of spring units loading said members.

8. The rotary rheometer according to claim 1,
further comprising a holder fora measurement or drive motor;
wherein said force circuit has individual components including a carrier and a carrier plate of the measurement or drive motor;
wherein one of said measurement parts has a measurement shaft;
wherein said adjustment device has a drive spindle; and
wherein said switching contacts are disposed on at least one of said individual components of said force circuit along said measurement shaft, along said drive spindle of said adjustment device, along said holder, between said individual components or in a transition region between said individual components.

9. The rotary rheometer according to claim 1, wherein said force circuit further has a stand, a frame, a spindle, a spindle drive, a carrier for a drive or measurement motor, a measurement shaft, one of said measurement parts, and said adjustment device for a height adjustment of at least one of said one measurement part, said spindle or said spindle drive.

10. The rotary rheometer according to claim 1, wherein said adjustment device abruptly terminates an adjustment movement of said measurement parts relative to one another when said switching contacts are opened.

11. The rotary rheometer according to claim 1,
further comprising a device for measuring a normal force; and
wherein in order to detect at least one of said measurement parts in a course of an adjustment by a force exerted by a sample, in addition to said switching unit or said switching contacts responding to the force flow in said force circuit, said device measures the normal force exerted by the sample and directed positively or negatively with respect to a direction of the force flow.

12. The rotary rheometer according to claim 1, further comprising:
a lifting spring and a lowering spring being respectively pre-stressed with a pre-stressed force or a limit force value, which corresponds to a weight of components or an apparatus to be carried of the rotary rheometer and a predetermined force value, the predetermined force value corresponding to a force value exerted by a sample onto one of said measurement parts in positive and negative directions of the force flow and still regarded as tolerable.

13. The rotary rheometer according to claim 1, said switching contacts each have a component extending parallel to the predetermined movement direction.

14. A rotary rheometer, comprising:
an adjustment device;
two measurement parts delimiting a measurement gap and can be moved relative to one another in a predetermined movement direction by said adjustment device;
a force circuit delimited by said measurement parts;
at least one switching unit responding to changes in a force flow in said force circuit, said switching unit having switching contacts for an activation of said adjustment device, said switching unit stopping said adjustment device when a predetermined limit force value is exceeded for the force flow in a positive or negative direction, without relative movement of said measurement parts, or with said measurement parts remaining in a same position;

an annular contact member with an upwardly projecting contact part;

said adjustment unit having a drive spindle and a nut mounted adjustably in height on said drive spindle, said nut carrying said annular contact member with said upwardly projecting contact part;

a clamping ring;

a clamp sleeve having a lower end carrying said clamping ring;

a contact part formed by a contact ring lying above said upwardly projecting contact part and being connected to said clamp sleeve;

a measurement shaft;

said force circuit having a carrier of a drive or measurement motor;

a coil spring with a predetermined spring force being disposed between said clamping ring and said carrier or of said measurement shaft; and a further coil spring with a predetermined spring force being disposed between said nut and said clamping ring.

15. A rotary rheometer, comprising:

an adjustment device;

two measurement parts delimiting a measurement gap and can be moved relative to one another in a predetermined movement direction by said adjustment device;

a force circuit delimited by said measurement parts;

at least one switching unit responding to changes in a force flow in said force circuit, said switching unit having switching contacts for an activation of said adjustment device, said switching unit stopping said adjustment device when a predetermined limit force value is exceeded for the force flow in a positive or negative direction, without relative movement of said measurement parts, or with said measurement parts remaining in a same position;

said adjustment unit having a drive spindle and a nut mounted adjustably in height on said drive spindle;

said force circuit having a carrier carrying an upwardly projecting contact part;

a contact member with a downwardly projecting contact part, which can be applied from above onto said upwardly projecting contact part carried by said carrier, is disposed above said carrier;

a clamping sleeve carrying said upwardly projecting contact part and having a lower end;

a clamping ring being carried by said clamping sleeve at said lower end;

a measurement shaft;

a coil spring with a predetermined spring force being disposed between said clamping ring and said carrier of a drive or measurement motor or of said measurement shaft; and a further coil spring with a further predetermined spring force being disposed between said nut and said clamping ring.

16. The rotary rheometer according to claim 15, said coil spring encloses said further coil spring and extends below one of said switching contacts.

17. The rotary rheometer according to claim 15, said clamping sleeve lies between said coil spring and said further coil spring.

18. The rotary rheometer according to claim 15, said further coil spring encloses said drive spindle.

* * * * *